United States Patent [19]

Richard

[11] Patent Number: 5,029,447
[45] Date of Patent: Jul. 9, 1991

[54] MULTICHAMBER STORAGE APPARATUS AND RELATED METHOD

[75] Inventor: Daniel D. Richard, Sedona, Ariz.

[73] Assignee: Cryo-Cell International Inc., Baldwin, N.Y.

[21] Appl. No.: 535,414

[22] Filed: Jun. 8, 1990

Related U.S. Application Data

[63] Continuation-in-part of Ser. No. 389,543, Aug. 4, 1989, Pat. No. 4,969,336.

[51] Int. Cl.$^5$ .............................................. F25D 13/04
[52] U.S. Cl. ........................................... 62/63; 62/65; 62/441
[58] Field of Search ..................... 62/63, 65, 265, 266, 62/373, 440, 441

[56] References Cited

U.S. PATENT DOCUMENTS

| | | |
|---|---|---|
| 1,938,985 | 12/1933 | Starr . |
| 2,599,173 | 6/1952 | Hamilton . |
| 2,928,705 | 3/1960 | Goldsmith . |
| 2,950,605 | 8/1960 | Hennion . |
| 3,034,845 | 5/1962 | Haumann . |
| 3,141,123 | 7/1964 | Olson . |
| 3,287,925 | 11/1966 | Kane et al. ............................ 62/52.1 |
| 3,455,120 | 7/1969 | Schlemmer ............................ 62/65 |
| 3,583,171 | 6/1971 | Flynn et al. . |
| 3,699,631 | 10/1972 | Valdes . |
| 3,942,334 | 3/1976 | Pink . |
| 4,124,992 | 11/1978 | Chmiel . |
| 4,199,022 | 4/1980 | Senkan et al. . |
| 4,304,293 | 12/1981 | Schiewe et al. . |
| 4,314,459 | 2/1982 | Rivoire . |
| 4,340,263 | 7/1982 | Webb . |
| 4,480,682 | 11/1984 | Kaneta et al. . |
| 4,531,373 | 6/1985 | Rubinsky . |
| 4,627,799 | 12/1986 | Terauchi . |
| 4,681,839 | 7/1987 | Swartz . |
| 4,712,607 | 12/1987 | Lindemans et al. . |
| 4,713,941 | 12/1987 | Toyoda et al. . |
| 4,790,141 | 12/1988 | Glascock . |
| 4,870,829 | 3/1989 | Oullette . |

Primary Examiner—Ronald C. Capossela
Attorney, Agent, or Firm—R. Neil Sudol; Henry D. Coleman

[57] ABSTRACT

A storage apparatus comprises a housing defining a plurality of chambers disposed one next to the other, the housing including partitions for separating the chambers from one another. Temperature control components are provided for controlling temperature independently in each of the chambers. Access openings are provided in the partitions between the chambers for enabling communication between each chamber and the chamber of chambers contiguous therewith. A support member movably supports a plurality of specimen-containing receptacles within the housing, while a drive is operatively connected to the support member for moving the receptacles from chamber to chamber through the access openings. An access door in the housing enables deposition and removal of a selected one of the receptacles from the housing.

32 Claims, 5 Drawing Sheets 5,029,447

MULTICHAMBER STORAGE APPARATUS AND RELATED METHOD

CROSS-REFERENCE TO A RELATED APPLICATION

This application is a continuation-in-part of application Ser. No. 389,543, filed Aug. 4, 1989, now U.S. Pat. No. 4,969,336.

BACKGROUND OF THE INVENTION

This invention relates to a storage apparatus, particularly a low-temperature storage apparatus.

It is well known to use liquid nitrogen in the short-term and long-term storage of biological materials such as blood cells and micro-organisms. The storage is meant to preserve the biological integrity of cellular tissues and organisms for future therapeutic use and research.

Liquid nitrogen is used in part because it is has a relatively low boiling point. Owing to difficulties in manufacture, however, liquid nitrogen is a very expensive substance.

OBJECTS OF THE INVENTION

An object of the present invention is to provide an improved method for storing perishable items.

A more particular object of the present invention is to provide a method and a related apparatus for low temperature storage of specimens, particularly biological specimens.

Another object of the present invention is to provide such a method and apparatus wherein the costs associated with the use of liquid nitrogen as a coolant are reduced, while retaining at least to some extent the low temperatures characteristically attainable through the use of liquid nitrogen.

Another particular object of the present invention is to provide such a method and apparatus which provides for use of several coolants.

SUMMARY OF THE INVENTION

A storage apparatus comprises, in accordance with the present invention, a housing defining a plurality of chambers disposed one next to the other, the housing including partitions for separating the chambers from one another. Temperature control components are provided for controlling temperature independently in each of the chambers. Access openings are provided in the partitions between the chambers for enabling communication between each chamber and the chamber of chambers contiguous therewith. A support member movably supports a plurality of specimen-containing receptacles within the housing, while a drive is operatively connected to the support member for moving the receptacles from chamber to chamber through the access openings. An access door in the housing enables deposition and removal of a selected one of the receptacles from the housing.

Pursuant to a feature of the present invention, the chambers are disposed in a substantially annular configuration. Alternatively, the chambers are disposed in a substantially linear configuration.

Preferably, the temperature control components include a plurality of different coolants and cooling devices for cooling each of the chambers with a respective one of the coolants. The access door is preferably disposed at the chamber with a highest temperature.

Pursuant to another feature of the present invention, the access openings are formed with seals to restrict movement of the coolants between the chambers. The seals may take the form of flexible sealing members disposed at locations between the cooling chambers. As an additional measure, intermediate spaces between the chambers are connected to one or more pumps for evacuating coolant material from the interchamber spaces. Alternatively, the interchamber spaces may be connected to pressure sources for pressurizing the spaces and thereby inhibiting the different coolants from penetrating beyond their respective chambers.

The temperature control components advantageously include an L-shaped coolant container in at least one of the chambers. The L-shaped coolant chambers contain liquid coolant such as liquid nitrogen.

Pursuant to another feature of the present invention, the drive serves to move the receptacles from a warmest chamber to a coldest chamber and subsequently back to the warmest chamber. In addition, the chambers may include a middle chamber located between the warmest chamber and the coldest chamber, the middle chamber having an intermediate temperature. In this case, the drive serves to move the receptacles from the warmest chamber to the coldest chamber and back to the warmest chamber through the middle chamber.

Pursuant to yet another feature of the present invention, the drive includes conveyor means for moving the support member, together with the plurality of receptacles, in at least one of the chambers along a path including a snaking portion, the snaking portion having a plurality of vertically extending folds.

Pursuant to a further feature of the present invention, a tracking device is operatively connected to the drive for automatically tracking the positions of the plurality of receptacles during motion thereof along a path through the chambers.

In accordance with an additional feature of the present invention, an extraction mechanism is disposed outside of the housing at the access door for removing a selectable one of the receptacles positioned in the housing in juxtaposition to the access door. Moreover, a selector such as a keyboard may be provided outside of the housing for enabling a selection among the receptacles by an operator.

Where the drive includes a conveyor for moving the support member, together with the plurality of receptacles, in at least one of the chambers along a predetermined path, and where the storage apparatus further comprises the tracking device, the extraction mechanism and the selector, a control is operatively connected to the selector, the tracking device, the conveyor and the extraction mechanism for operating the conveyor, upon selection of a given one of the receptacles via the selector, to move the given one of the receptacles along the path to the access door, and for operating the extraction mechanism to remove the given one of the receptacles from the support member and out through the access door.

A method for storing a perishable specimen comprises, in accordance with the present invention, the steps of: (a) inserting the specimen in a first chamber having a first temperature, (b) maintaining the specimen for at least a first predetermined period in the first chamber, (c) automatically moving the specimen, upon termination of the first predetermined period, from the first chamber to a second chamber having a second temperature, (d) maintaining the specimen for at least a second predetermined period in the second chamber, (e) subsequent to the termination of the second predetermined period, automatically moving the specimen from the second chamber back to the first chamber, (f) repeating steps (b) through (e) until the specimen is required for utilization, and (g) removing the specimen from the chambers upon requirement of the specimen for utilization.

Pursuant to another feature of the present invention, the first temperature is lower than room temperature and the second temperature is lower than the first temperature. Generally, the specimen is cooled prior to insertion thereof into the first chamber and, more specifically, is cooled substantially down to the second temperature. However, in some circumstances the cooling of the specimen is accomplished in the first chamber.

Preferably, the first chamber is cooled with a first coolant and the second chamber is cooled with a second coolant different from the first coolant. The lower temperature coolant may, for instance, take the form of liquid nitrogen, while the higher temperature coolant takes the form of a chlorofluorocarbon.

Also, the specimen is preferably moved along a predetermined path between the first chamber and the second chamber, that path including a snaking portion.

DETAILED DESCRIPTION

Figure 1:
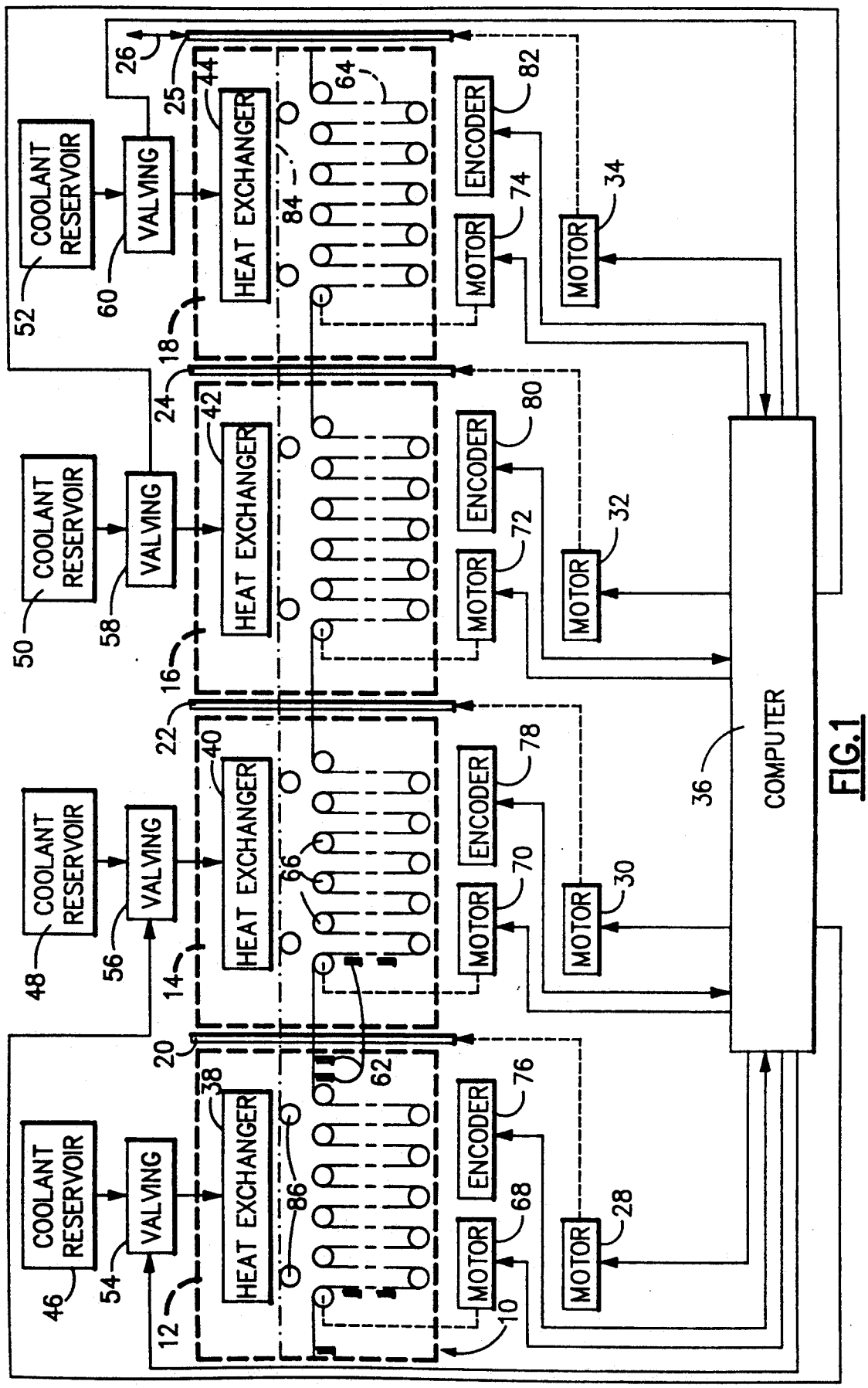
FIG. 1 is block diagram, with schematic representations, of a multichamber storage apparatus in accordance with the present invention.

As illustrated in FIG. 1, a multichamber storage apparatus comprises a housing 10 defining a plurality of chambers 12, 14, 16 and 18 disposed one adjacent to the other. Chambers 12, 14, 16, and 18 represent a portion of a larger number of chambers arranged preferably in an endless array. However, the chambers of the multichamber storage apparatus may also be arranged in a linear array, as described hereinafter with reference to FIGS. 2 and 3.

Housing 10 includes a plurality of partitions 20, 22, 24 and 25 which separate chambers 12, 14, 16, and 18 from one another. Partitions 20, 22, 24 and 25 take the form of movable door members which are shiftable in the direction of arrow 26 by respective motor drives 28, 30, 32 and 34 acting under the control of a computer 36.

Each chamber 12, 14, 16, and 18 is provided with a respective heat exchanger unit 38, 40, 42 and 44 which communicates with a respective coolant reservoir 46, 48, 50 and 52 through a respective valve device 54, 56, 58 and 60 which is operated by computer 36. Heat exchanger units 38, 40, 42 and 44 may take any form suitable for providing the respective chamber 12, 14, 16, and 18 with a predetermined temperature. Concomitantly, the coolants contained in reservoirs 46, 48, 50 and 52 and circulated to heat exchanger units 38, 40, 42 and 44 under the control of computer 36 are different compositions having different cooling temperatures. For example, chamber 14 may be cooled by liquid nitrogen, while chambers 12 and 16 are cooled by a chlorofluorocarbon of one composition and chamber 18 by a chlorofluorocarbon of another, different composition having a boiling point different from the boiling point of the first chlorofluorocarbon composition. In that case, the boiling point of the chlorofluorocarbon coolant in reservoirs 46 and 50 is preferably lower than the boiling point of the coolant in reservoir 52.

Operating valve devices 54, 56, 58 and 60, computer 36 controls the temperatures of chambers 12, 14, 16, and 18. The temperature in each chamber is independent of the temperatures in the other chambers and is determined to a large extent by the boiling point of the respective coolant. The exact temperature may be varied through the action of computer 36 in response to non-illustrated temperature sensors located, for example, in each chamber 12, 14, 16, and 18.

As shown in FIG. 1, a multiplicity of specimen-containing receptacles 62 are supported on a pair of endless chains 64 (visible as only one chain in dot-dash line in the drawing) extending from one chamber 12, 14, 16, and 18 to the next. Chains 64 are in turn supported by a plurality of pulleys 66 to define in each chamber 12, 14, 16, and 18 a snaking path having a plurality of vertically oriented folds. A plurality of drive motors 68, 70, 72, and 74 are connected to respective driven pulleys for moving the chains and their receptacle payload along the snaking paths and from chamber to chamber.

Chains 64 and the details of the structure (e.g., bars) by which receptacles 62 are supported from chains 64 are described in commonly owned U.S. patent application Ser. No. 389,543 filed Aug. 4, 1989 now U.S. Pat. No. 4,969,336, the disclosure of which is hereby incorporated by reference. That prior application also discloses a mechanism for inserting and removing receptacles 62 individually from a cryogenic storage chamber. The same mechanism is used in the apparatus of FIG. 1. Preferably, the receptacle insertion and removal mechanism is placed at one chamber 12, 14, 16, or 18 only, most preferably a chamber having a highest temperature. However, in some applications it may be advantageous to insert and retrieve receptacles 62 from a plurality of chambers among chambers 12, 14, 16, and 18, for example, to facilitate and accelerate the insertion and retrieval process.

As described in application Ser. No. 389,543, computer 36 tracks the locations of receptacles 62 during their travels through housing 10 via signals received from one or more encoders 76, 78, 80 and 82 operatively linked to pulleys 66 for monitoring the motion of chains 64. Computer 36 is also connected to drive motors 68, 70, 72 and 74 and to the insertion and retrieval mechanism(s) for controlling the operations thereof. As disclosed in prior U.S. Pat. No. 4,969,336, a keyboard or other input device (not illustrated herein) may be connected to computer 36 for instructing the computer to remove a certain receptacle from the multichamber storage apparatus. The computer determines the location of the requested receptacle from its memory whose contents are continuously updated by input from encoders 76, 78, 80 and 82.

As indicated diagrammatically in FIG. 1 by a dot-dash line 84 and pulley-representing circles 86, the path along which receptacles 62 are moved through housing 10 is an endless path. The receptacles may return to a starting position via a return path 84 which passes through the same chambers 12, 14, 16, and 18 (see FIGS. 2 and 3) or through different chambers (see FIGS. 4 and 5).

Upon shifting under the action of motor drives 28, 30, 32 and 34, partitions or door members 20, 22, 24 and 25 define access openings for enabling communication between each chamber 12, 14, 16, and 18 and at least one other chamber contiguous therewith. Partitions or door members 20, 22, 24 and 25 move swiftly and open no further and no longer than necessary to allow the passage of a bar (see application Ser. No. 389,543) or bank of receptacles 62 from one chamber 12, 14, 16, or 18 to the next.

Figure 2:
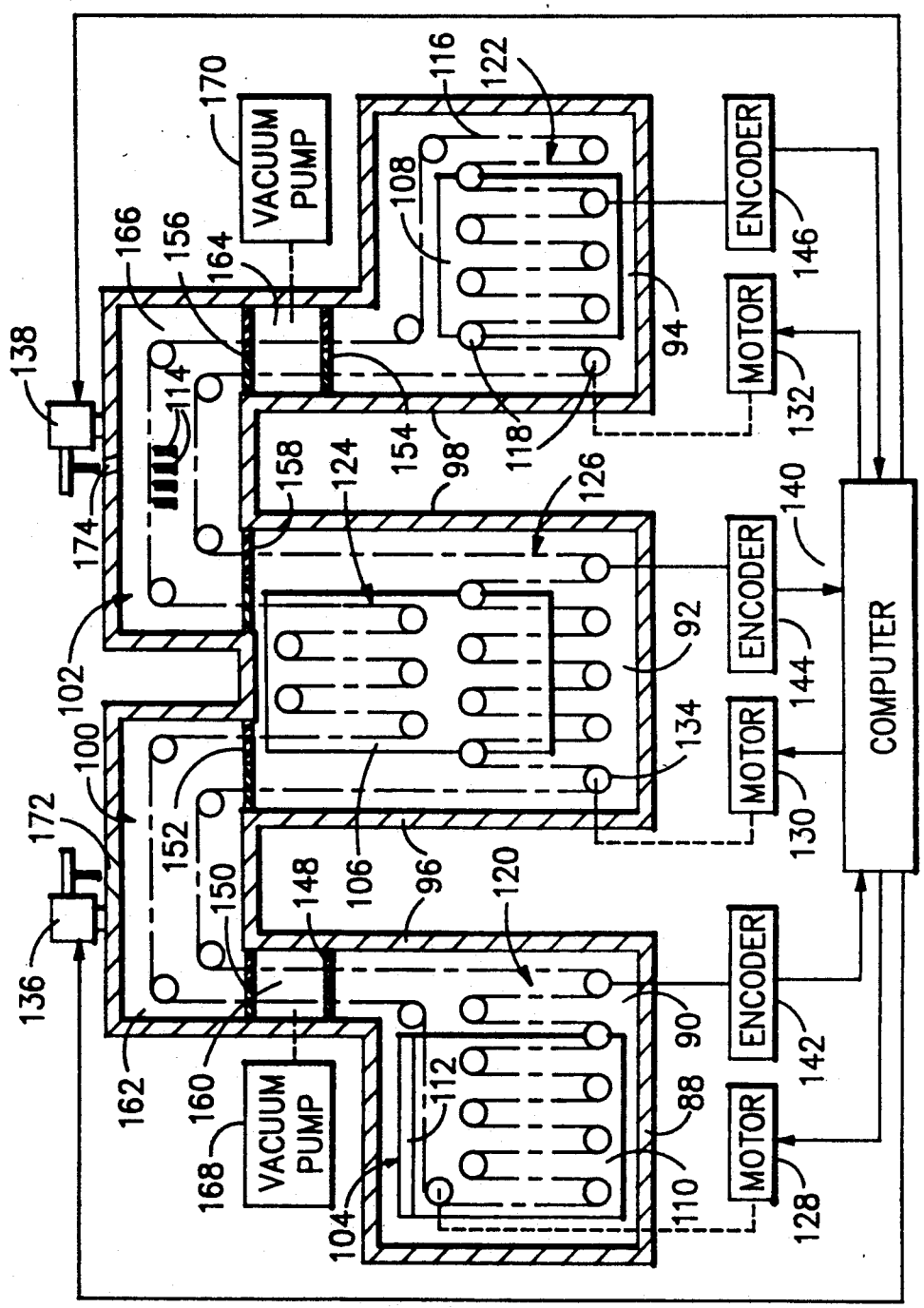
FIG. 2 is partially a block diagram and partially a schematic cross-sectional view of another multichamber storage apparatus in accordance with the present invention.

As depicted in FIG. 2, another multichamber storage apparatus comprises a housing 88 defining three separate storage chambers 90, 92 and 94 disposed in a linear array in juxtaposition with each other. Housing 88 includes a plurality of partition elements 96 and 98 separating chambers 90, 92 and 94 from each other and defining in part a plurality of openings or passageways 100 and 102 extending from one chamber to the next.

Each chamber 90, 92 and 94 is provided with a respective heat exchanger unit 104, 106 and 108. At least one unit, for example, heat exchanger unit 104, takes the form of an L-shaped coolant container with a vertically oriented leg 110 and a horizontally oriented leg 112 having an open face, as described in detail in U.S. Pat. No. 4,969,336 incorporated by reference herein. Preferably, L-shaped coolant container 104 holds liquid nitrogen which sublimates off in a vaporous form to fill chamber 90, while heat exchanger units 106 and 108 contain liquid coolants such as chlorofluorocarbons which have higher boiling points than that of liquid nitrogen.

A multiplicity of specimen-containing receptacles 114 are supported on a pair of endless chains 116 (visible as only one chain in dot-dash line in the drawing) extending from chamber 90 to chamber 94 through chamber 92 and back again. Chains 116 are partially wound about a plurality of pulleys 118 to define a snaking path having one group of vertically oriented folds 120 and 122 in each chamber 90 and 94 and two groups of vertically oriented folds 124 and 126 in chamber 92. A plurality of drive motors 128, 130 and 132 are connected to respective driven pulleys 134 for moving chains 116 and their receptacle payload along the snaking path and from chamber to chamber.

The multichamber storage apparatus of FIG. 2 is provided with a pair of receptacle insertion and retrieval mechanisms 136 and 138 such as that described in detail in U.S. Pat. No. 4,969,336. Insertion and retrieval mechanisms 136 and 138 are mounted on portions of housing 88 above passageways 100 and 102. Chains 116 and the details of the structure (e.g., bars) by which receptacles 114 are supported from chains 116 are also described in application Ser. No. 389,543.

A computer 140 tracks the locations of receptacles 114 during their motion through housing 88 via signals received from one or more encoders 142, 144 and 146 operatively linked to pulleys 118 for monitoring the motion of chains 116. Computer 140 is also connected to drive motors 128, 130 and 132 and to insertion and retrieval mechanisms 136 and 138 for controlling the operations thereof. As set forth in prior U.S. Pat. No. 4,969,336, a keyboard or other input device (not illustrated herein) may be connected to computer for instructing the computer to remove a certain receptacle from the multichamber storage apparatus. The computer determines the location of the requested receptacle from its memory whose contents are continuously updated by input from encoders 142, 144 and 146.

As shown in FIG. 2, chambers 90 and 92 are separated from one another by sealing members 148, 150, and 152, and chambers 92 and 94 are separated from one another by sealing members 154, 156, and 158. Sealing members 148, 150 and 152 divide passageway 100 into a pair of buffer spaces 160 and 162, while sealing members 154, 156, and 158 divide passageway 102 into two intermediate spaces 164 and 166. Spaces 160 and 164 are connected to respective vacuum pumps 168 and 170 for evacuating those spaces of coolant which has penetrated from chambers 90 and 92. Spaces 162 and 166 are accessible by insertion and retrieval mechanisms 136 and 138 through slidable doors 172 and 174 (see U.S. Pat. No. 4,969,336.

Sealing members 148, 150, 152 and 154, 156, 158 take the form of a multiplicity of parallel resilient fingers formed by cutting along parallel lines in a strip of flexible elastic material such as synthetic rubber. The fingers allow the traversal of the sealing members continuously by chains 116 and periodically by receptacles 114 and the support bars (see Ser. No. 389,543) thereof.

Cooling vapors or gases which have penetrated into spaces 160 and 164 and which are evacuated from those spaces by vacuum pumps 168 and 170 are replaced in chambers 90, 92 and 94 by sublimating vapors from heat exchanger units 104, 106 and 108. Alternatively, heat exchanger units 106 and 108, represent closed systems wherein the operative coolant material is not permitted to escape into chambers 92 and 94. In that case, vacuum pumps 168 and 170 are dispensed with and chambers 92 and 94 are filled with a gas such as nitrogen which is cooled by the respective heat exchanger units 106 and 108 to respective temperature levels higher than nitrogen's boiling point. Sealing members 148, 150, 152 and 154, 156, 158 then serve to prevent or at least inhibit the mixing of the nitrogen gas at the different temperatures.

Figure 3:
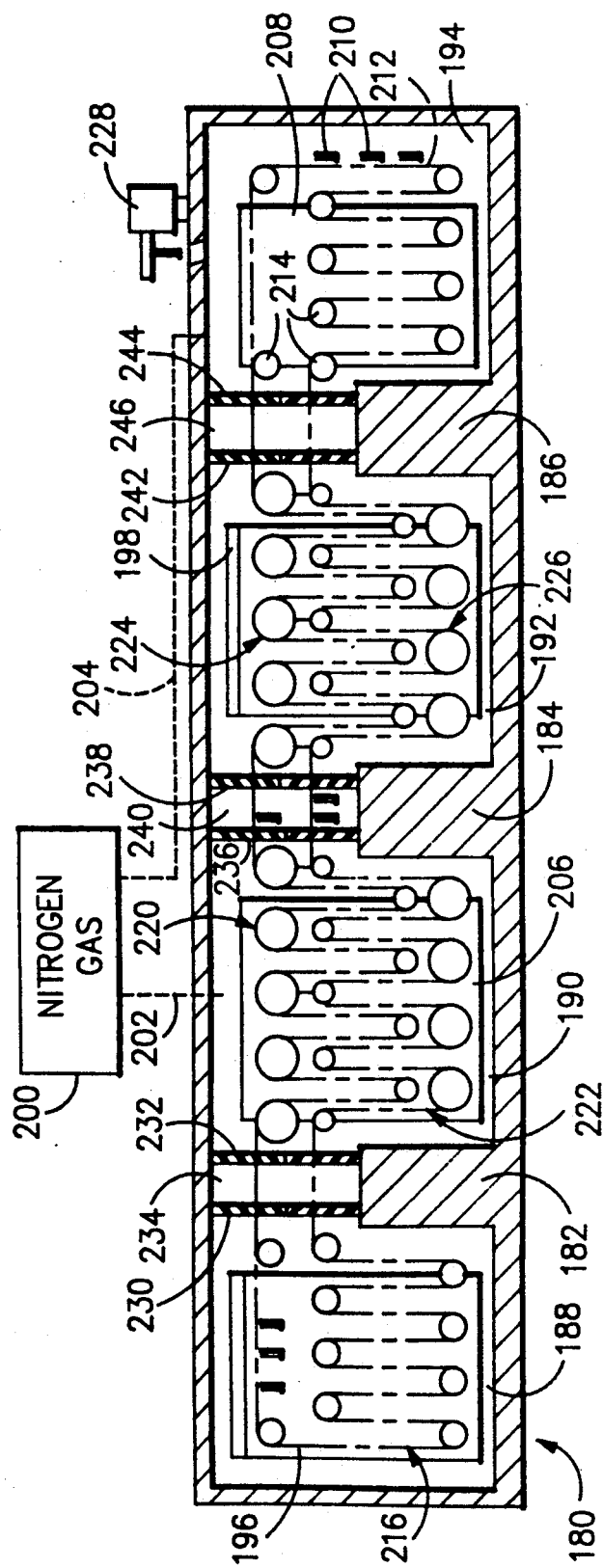
FIG. 3 is a partially cross-sectional view of another multichamber storage apparatus in accordance with the present invention.

As illustrated in FIG. 3, another multichamber storage apparatus comprises a housing 180 and partition members 182, 184 and 186 which define a plurality of storage chambers 188, 190, 192 and 194. Storage chambers 188, 190, 192 and 194 are filled with gaseous nitrogen. In chambers 188 and 190, the nitrogen vapor is generated by a pool of liquid nitrogen stored in a respective L-shaped coolant reservoir or tank 196 and 198 having an open upper face, as described in application Ser. No. 389,543. In chambers 190 and 194, gaseous nitrogen is supplied from an external storage tank 200 and fed to chambers 190 and 194 via conduits 202 and 204. In chambers 190 and 194, the gaseous nitrogen is cooled to temperatures exceeding the boiling point of liquid nitrogen by respective closed-loop heat exchanger units 206 and 208 containing a coolant such as a chlorofluorocarbon. Chambers 190 an 194 may be cooled to approximately the same temperature, the coolant in heat exchanger units 206 and 208 being the same composition. It is to be understood that several higher temperature storage chambers may be disposed between chambers 188 and 192.

A multiplicity of specimen-containing receptacles 210 are supported on a pair of endless chains 212 (visible as only one chain in dot-dash line in the drawing) extending from chamber 188 to chamber 194 through chambers 190 and 192 and back again. Chains 212 are partially wound about a plurality of pulleys 214 to define a snaking path having one group of vertically oriented folds 216 and 218 in each chamber 188 and 194 and two groups of vertically oriented folds 220, 222 and 224, 226 in each chamber 190 and 192. A plurality of drive motors (not shown) are connected to respective driven pulleys (not designated) for moving chains 212 and their receptacle payload along the snaking path and from chamber to chamber.

The multichamber storage apparatus of FIG. 3 is provided with at least one receptacle insertion and retrieval mechanism 228 such as that described in detail in U.S. Pat. No. 4,969,336. Insertion and retrieval mechanism 228 is mounted on housing 88 above chamber 194. Chains 212 and the details of the structure (e.g., bars) by which receptacles 210 are supported from chains 212 are also described in U.S. Pat. No. 4,969,336.

As shown in FIG. 3, chambers 188 and 190 are separated from one another by sealing members 230 and 232 which are distanced from one another to form a buffer space 234. Similarly, chambers 190 and 192 are spearated from one another by a pair of sealing members 236 and 238 which define an interchamber buffer space 240, while chambers 199 and 194 are divided from one anothe by two sealing members 242 and 244 which define a sealing space 250.

Sealing members 230, 232, 236, 238, 242 and 246 each take the form of a pair of strips of resilient flexible material such as rubber cut along multiplicity of parallel lines to form a multiplicity of resilient fingers. The fingers allow the traversal of the sealing members continuously by chains 212 and periodically by receptacles 210 and the support bars (see U.S. Pat. No. 4,969,336) thereof.

Computer control of the movement of chains 212 and the operation of insertion and retrieval mechanism 228 is implemented as described above with reference to FIGS. 1 and 2.

Figure 4:
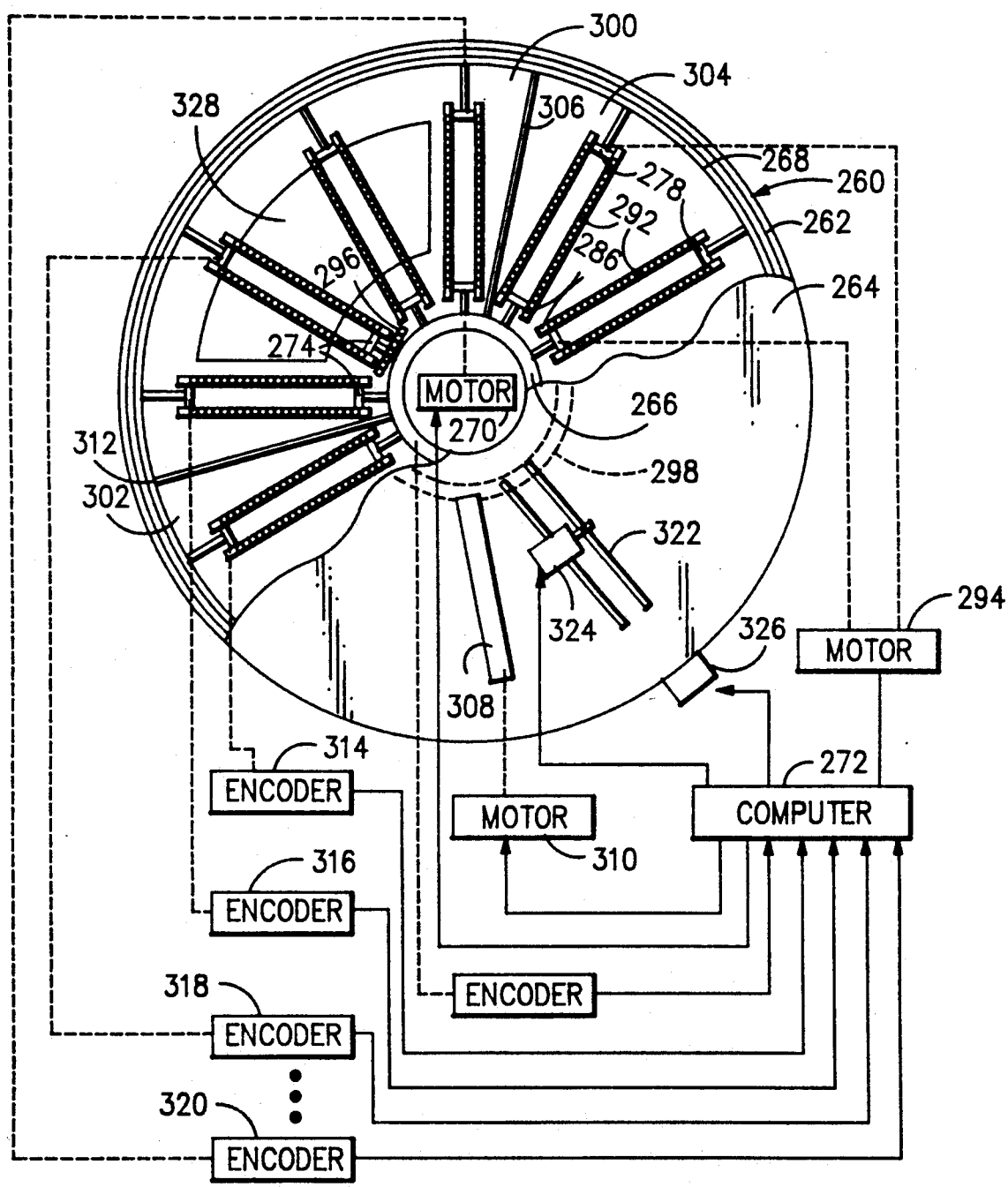
FIG. 4 is partially a block diagram, partially a schematic cross-sectional view and partially a top view of yet another multichamber storage apparatus in accordance with the present invention.

As illustrated in FIG. 4, another multichamber storage apparatus comprises a housing 260 including a cylindrical outer wall 262 and a disk shaped upper wall 264. Disposed inside housing 260, coaxial with cylindrical outer wall 262 thereof is a an inner cylindrical drive member 266 and an outer cylindrical drive member 268. Drive members 266 and 268 are rotated about their axis of symmetry at a susbtantially constant velocity by a drive motor 270 which may be alternately energized and de-energized by a computer 272.

Figures 5, 6:
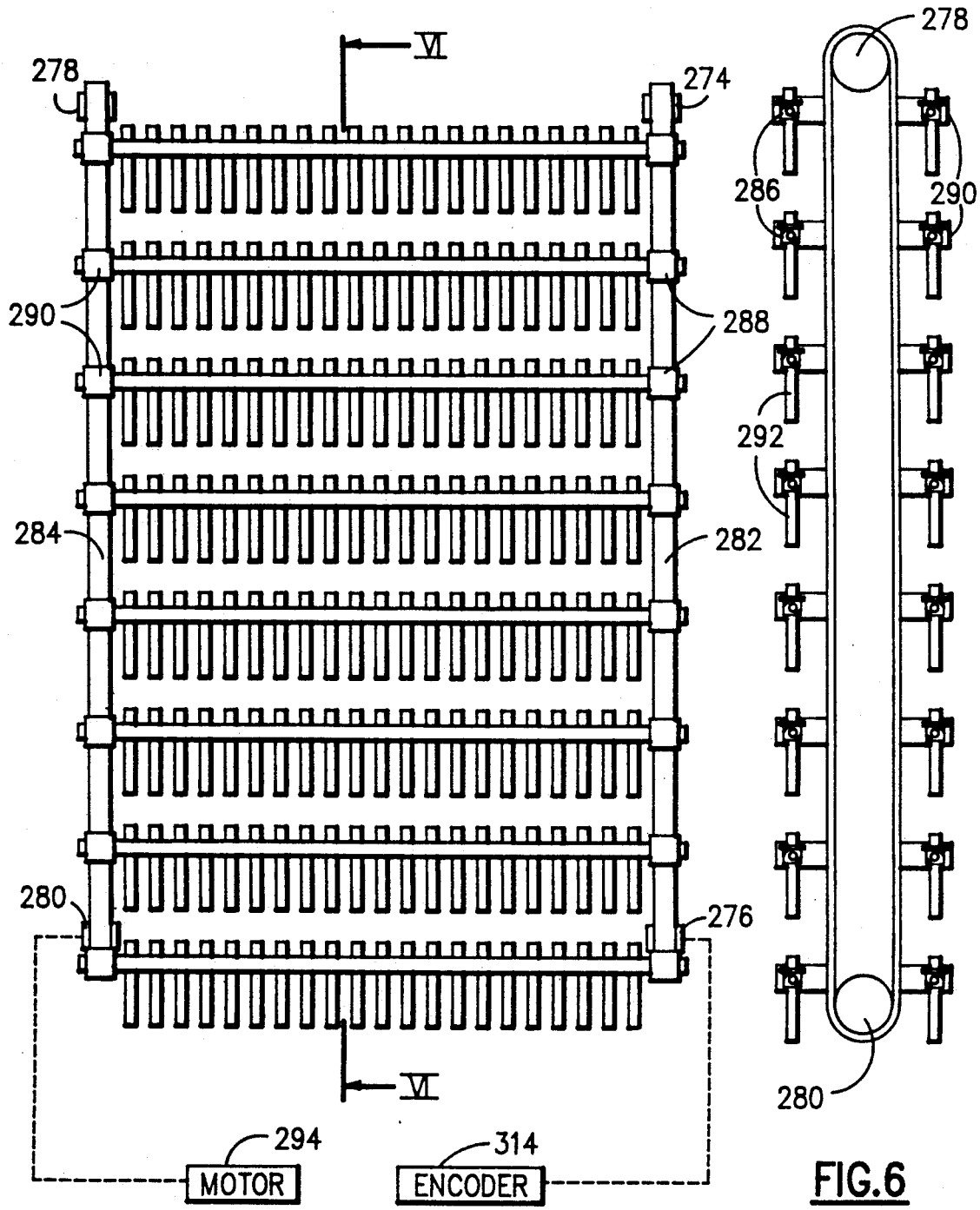
FIG. 5 is a schematic front elevational view of a bank of specimen-containing receptacles and support elements in the multichamber storage apparatus of FIGS. 4 and 5.
FIG. 6 is a schematic side elevational view of the specimen-containing receptacles and support elements of FIG. 6.

As shown in FIGS. 4, 5 and 6, inner drive member 266 carries a plurality of circumferentially spaced upper drive pulleys 274 and a plurality of circumferentially spaced lower drive pulleys 276, pulleys 274 and 276 being disposed in circular arrays longitudinally spaced from one another. Similarly, outer drive member 268 carries a plurality of circumferentially spaced upper drive pulleys 278 and a plurality of circumferentially spaced lower drive pulleys 280 disposed in two circular arrays longitudinally spaced from one another. Each pulley 274, 276, 278 and 280 is mounted to drive member 266 or 268 for rotation about an axis oriented radially with respect to housing wall 262, inner drive member 266 and outer drive member 268.

Each lower inner pulley 276 is drivingly coupled to a respective upper inner pulley 274 via a respective endless belt or chain 282 (FIG. 5), while each lower outer pulley 280 is drivingly linked to a respective upper outer pulley 278 via another endless belt or chain 284. Each inner belt or chain 282 and an associated outer belt or chain 284 carries a plurality of bars 286 each pivotably attached to the inner belt 282 via a first bracket 288 and pivotably secured to the outer belt 284 via a second bracket 290. Each bar 286 is provided with a row of equispaced openings (not shown) for receiving a plurality of specimen-containing receptacles or vials 292.

As indicated schematically in FIG. 4, at least one of each set of four pulleys 274, 276, 278 and 280 coupled to one another by belts 282 and 284 and bars 286 is driven in a rotary mode by a motor 294 operated under the control of computer or microprocessor 272. In an alternative or complementary drive system, each gang of coupled pulleys 274, 276, 278 and 280 is provided with a toothed drive gear 296 which meshingly engages a toothed ring 298 fastened to an inner surface of disk 264.

Motor 294 or gear 296 and ring 298 cause bars 286 and receptacles 292 to be moved up and down in a longitudinal direction, while motor 270 drives the specimen-containing receptacles and their supporting bars along a circular path through housing 260. The resulting motion is along a zig-zag or spiraling path. That path extends through a plurality of cooling chambers 300, 302 and 304 separated from one another by a plurality of door members 306 each in the form of a flexible web or sheet mounted to a respective coil housing 308 in turn disposed atop disk 264. Door members 306 are alternately opened and closed by respective motors 310 (only one shown) under the control of computer 272. Door members 306 have vertially extending edges 312 which deformably and slidingly engage an inner surface of outer drive member 268 or an inner surface of housing wall 262.

As illustrated in FIG. 4, computer 272 receives digitized information from a plurality of encoders 314, 316, 318, 320 . . . each operatively connected to a respective inner or outer belt 282 or 284 for enabling computer 272 to track the locations of receptacles 292 during their spiraling or zig-zag motion through housing 260.

Upon receiving an instruction from an operator to retrieve a certain receptacle 292, computer 272 operates motors 270 and 294 to move the receptacle into position below a radially extending door 322 in disk 264. Computer 272 then opens the door 322 and activates a receptacle insertion and retrieval mechanism 324 to remove the selected receptacle and deposit it in an enclosure 326, as described in application Ser. No. 389,543.

Each chamber 300, 302 and 304 is provided with a respective cooling system or heat exchanger unit 328 (only one shown in the drawing). As described hereinabove with reference to FIGS. 1-3, each chamber 300, 302 and 304 is cooled to a respective low temperature by means of a chemically different coolant composition. One coolant may be liquid nitrogen while other coolants are chlorofluorocarbons.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A storage apparatus comprising:
    housing means for defining a plurality of chambers disposed one next to the other, said housing means including partition means for separating said chambers from one another;
    temperature control means for controlling temperature independently in each of said chambers;
    first access means for enabling communication between each one of said chambers and at least one other of said chambers contiguous with said one of said chambers;
    support means for movably supporting a plurality of specimen-containing receptacles within said housing means;
    drive means operatively connected to said support means for moving said receptacles from one to another of said chambers via said first access means; and
    second access means for enabling deposition and removal of a selected one of said receptacles from said housing means.

2. The apparatus according to claim 1 wherein said chambers are disposed in a substantially annular configuration.

3. The apparatus according to claim 1 wherein said chambers are disposed in a substantially linear configuration.

4. The apparatus according to claim 1 wherein said temperature control means includes a plurality of different coolants and cooling means for cooling each of said chambers with a respective one of said coolants.

5. The apparatus according to claim 4 wherein said second access means is disposed at one of said chambers having a highest temperature among said chambers.

6. The apparatus according to claim 4, further comprising closure means for providing a seal at said first access means to restrict movement of said coolants between said chambers.

7. The apparatus according to claim 6 wherein said closure means includes flexible sealing members disposed at locations between said chambers 8. The apparatus according to claim 6 wherein said closure means includes intermediate spaces between said chambers and pumping means for evacuating said spaces of coolant material.

9. The apparatus according to claim 6 wherein said closure means includes intermediate spaces between said chambers and pressurizing means for pressurizing said spaces.

10. The apparatus according to claim 6 wherein said first access means includes openings between said chambers and said closure means includes seals at said openings.

11. The apparatus according to claim 10 wherein said seals are movable door members.

12. The apparatus according to claim 10 wherein said seals are flexible passive elements.

13. The apparatus according to claim 1 wherein said temperature control means includes an L-shaped coolant container in at least one of said chambers.

14. The apparatus according to claim 13 wherein said L-shaped coolant chambers contains liquid coolant.

15. The apparatus according to claim 14 wherein said L-shaped coolant chambers contains liquid nitrogen.

16. The apparatus according to claim 1 wherein said drive means includes means for moving said receptacles from a warmest one of said chambers to a coldest one of said chambers and subsequently back to said warmest one of said chambers.

17. The apparatus according to claim 16 wherein said chambers include a middle chamber located between said warmest one of said chambers and said coldest one of said chambers, said middle chamber having an intermediate temperature, said drive means serving to move said receptacles from said warmest one of said chambers to said coldest one of said chambers and back to said warmest one of said chambers through said middle chamber.

18. The apparatus according to claim 1 wherein said temperature control means includes means for subjecting at least one of said chambers to a vacuum.

19. The apparatus according to claim 1 wherein said second access means includes an access door in said housing means and means operatively connected to said door for alternately opening and closing same.

20. The apparatus according to claim 1 wherein said drive means includes conveyor means for moving said support means, together with said plurality of receptacles, in at least one of said chambers along a path including a snaking portion, said snaking portion having a plurality of vertically extending folds.

21. The apparatus according to claim 1, further comprising tracking means operatively connected to said drive means for automatically tracking the positions of said plurality of receptacles during motion thereof along a path through said chambers.

22. The apparatus according to claim 1, further comprising extraction means disposed outside of said housing means at said second access means for removing a selectable one of said receptacles positioned in said housing means in juxtaposition to said second access means.

23. The apparatus according to claim 1, further comprising selection means outside of said housing means for enabling a selection of one of said receptacles by a operator.

24. The apparatus according to claim 23 wherein said drive means includes conveyor means for moving said support means, together with said plurality of receptacles, in at least one of said chambers along a predetermined path, further comprising:
    tracking means operatively connected to said drive means for automatically tracking the positions of said plurality of receptacles during motion thereof along said path;
    extraction means disposed outside of said housing means at said second access means for removing a selectable one of said receptacles positioned in said housing means in juxtaposition to said second access means; and
    control means operatively connected to said selection means, said tracking means, said conveyor means and said extraction means for operating said conveyor means, upon selection of a given one of said receptacles via said selection means, to move said given one of said receptacles along said path to said second access means, and for operating said extraction means to remove said given one of said receptacles from said support means and out through said second access means.

25. A method for storing a perishable specimen, comprising the steps of:
(a) inserting the specimen in a first chamber having a first temperature;
(b) maintaining said specimen for at least a first predetermined period in said first chamber;
(c) automatically moving said specimen, upon termination of said first predetermined period from said first chamber to a second chamber having a second temperature;
(d) maintaining said specimen for at least a second predetermined period in said second chamber;
(e) subsequent to the termination of said second predetermined period, automatically moving said specimen from said second chamber back to said first chamber;
(f) repeating steps (b) through (e) until said specimen is required for utilization; and
(g) removing said specimen from the chambers upon requirement of said specimen for utilization.

26. The method according to claim 25 wherein said first temperature is lower than room temperature and said second temperature is lower than said first temperature.

27. The method according to claim 26, further comprising the step of cooling said specimen prior to insertion thereof into said first chamber.

28. The method according to claim 26, further comprising the steps of cooling said first chamber with a first coolant and cooling said second chamber with a second coolant different from said first coolant.

29. The method according to claim 25 wherein said step of automatically moving includes the step of moving said specimen along a predetermined path between said first chamber and said second chamber.

30. The method according to claim 29 wherein said predetermined path includes a snaking portion.

31. The method according to claim 25 wherein said steps of inserting and removing are performed automatically.

32. The method according to claim 25, further comprising the step of automatically tracking the location of said specimen along said path.

* * * * *